United States Patent [19]

Bieganski et al.

[11] Patent Number: 4,905,709
[45] Date of Patent: Mar. 6, 1990

[54] DISPOSABLE TUBULAR PNEUMOTACHOMETER

[75] Inventors: Paul Bieganski, Minneapolis; Timothy E. Schweikert, Coon Rapids, both of Minn.

[73] Assignee: Advanced Medical Systems, Inc., Minneapolis, Minn.

[21] Appl. No.: 298,058

[22] Filed: Jan. 17, 1989

[51] Int. Cl.[4] .............................................. A61B 5/08
[52] U.S. Cl. .................................. 128/725; 73/861.52
[58] Field of Search ............... 128/716, 718, 719, 720, 128/725; 73/861.42, 861.52, 861.61

[56] References Cited

U.S. PATENT DOCUMENTS

| | | | |
|---|---|---|---|
| 1,759,239 | 5/1930 | Morrison | 73/861.52 |
| 3,504,542 | 4/1970 | Blevins | 128/725 |
| 3,792,609 | 2/1974 | Blair et al. | 73/861.52 |
| 3,840,051 | 10/1974 | Akashi et al. | 73/861.52 |

*Primary Examiner*—Kyle L. Howell
*Assistant Examiner*—K. M. Pfaffle
*Attorney, Agent, or Firm*—Jacobson and Johnson

[57] ABSTRACT

A disposable tubular pneumotachometer in which the air-resistive material covering over the air outlet is a fabric with multiple sub-miniature tubular apertures to provide capillary air flow and, in the preferred form, has a uniformly diverging air outlet formed by air outlet openings through the wall of the pneumotachometer tube and an imperforate proportionally tapered air-diverging surface facing the air outlet openings.

7 Claims, 1 Drawing Sheet

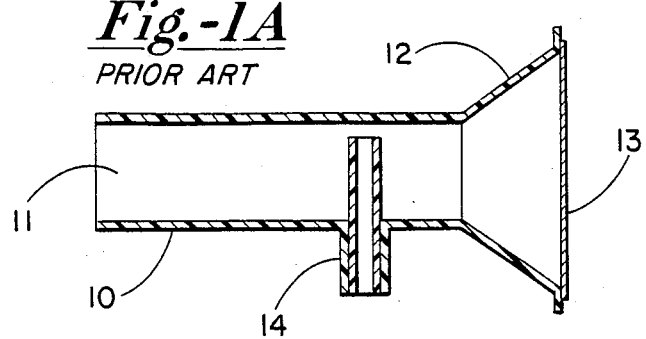
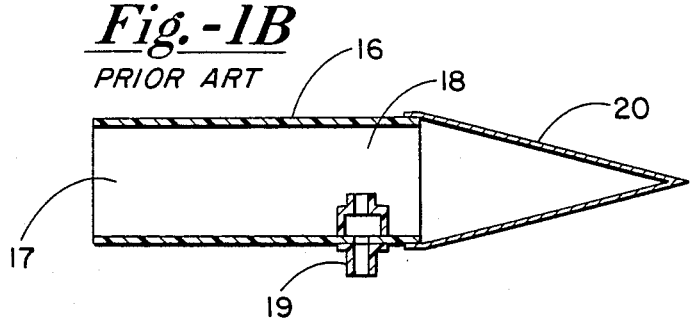
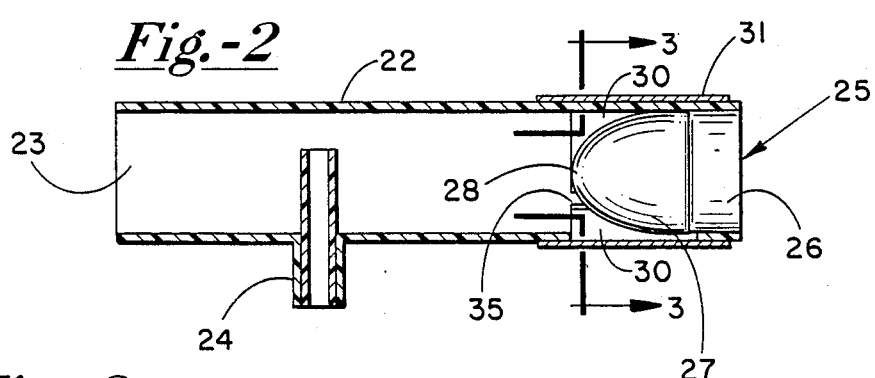
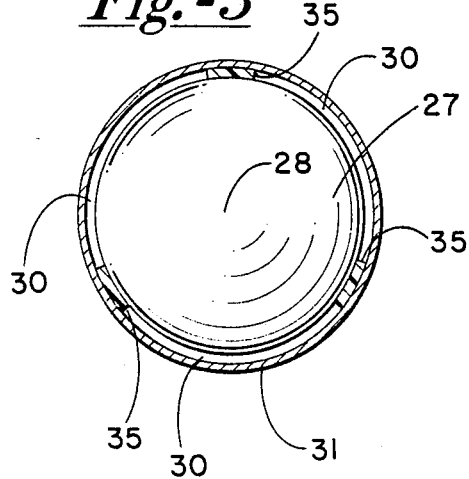
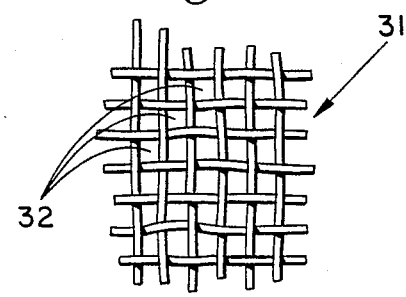

DISPOSABLE TUBULAR PNEUMOTACHOMETER

FIELD OF THE INVENTION

This invention is directed toward the field of measuring air flow and air volume discharged from human lungs during pulmonary functional testing (spirometry). More specifically, the invention is directed toward the design of a disposable device which may be referred to as a mouthpiece or pneumotachometer or flow sensor which a person blows into or breather into to provide a reading of pressure drop which is then utilized to give a measurement of the air flow and volume.

DESCRIPTION OF THE PRIOR ART

A number of articles and papers have been published over the years dealing with spirometry. In his *Manual of Pulmonary Function Testing*, 4th Edition, published by the C. V. Mosby Company in 1986, Gregg Ruppel, starting at page 147, describes various pulmonary testing equipment. Beginning at page 154, Ruppel described pneumotachometers which he defines as flow sensing devices which use "various physical principles to produce an analog output that can be integrated for measurement of volumes and flows". Amongst the pneumotachometers or flow sensors described by Ruppel is a pressure differential type which has an air-resistive element creating a pressure drop which is proportional to the flow of the gas or air through the tube in which the resistive element is located. A pressure transducer converts the pressure reading into electrical signals which can be integrated by suitable instrumentation to give air flow and volume readings. This is the type of testing device that the instant invention is directed toward.

In another publication titled *Pulmonary Function Testing Guidelines and Controversies* by Grune and Stratton, Inc. published by Harcourt, Brace, Jovanovich, copyright 1982, in Chapter 9 starting at page 91, is an article titled *Pneumotachography* by Dr. Arthur Dawson. Dr Dawson describes a pneumotachograph as "a device that measures instantaneous respiratory air flow". He goes on to say that "the most commonly used type is the differential pressure flow transducer, in which a sensitive manometer detects the pressure drop across a light resistance placed in the air stream". This substantially describes the flow sensor which the instant application is directed toward. Dr. Dawson goes on to describe a Fleisch pneumotachograph which utilizes capillary air flow resulting from the air flowing through a resistant element made up of a bundle of parallel capillary tubes in order to maintain a "linear relationship between flow and pressure difference". Dr. Dawson in another article titled *How To Make The Most Of Pneumotachography* appearing in the publication titled *Respiratory Management*, dated Jan./Feb. 1987 at page 46 goes on to explain that in a Fleisch pneumotachograph the resistive elements comprise one or more layers of fine metal screen and "when air flows through the resistance element, a small pressure gradient is generated which is measured with a sensitive manometer connected to ports on the upstream and downstream sides of the resistance". For all practical purposes, this is similar to the invention of the instant application except that the air flow is through a resistive element and exits to the atmosphere and since the pressure drop is measured with respect to atmospheric pressure, only a single pressure measurement point or takeoff is required between the air inlet and outlet.

While it appears that a pneumotachometer or flow sensor or mouthpiece containing an integrated bundle of metallized tubes to provide capillary air flow will provide the most accurate and reliable readings and, therefore, is most preferable, one pragmatic problem is that a flow sensor containing a resistive element of this nature becomes very costly. Because of the cost, it is not economically sound to make a disposable or throwaway flow sensor containing a resistive element of that nature, therefore a sensor of that nature is usually used over and over again but has to be sterilized between uses. Sterilization can affect the calibration of the flow sensor to the instrumentation with which it is used and therefore periodic recalibration may be necessary.

One commercially available disposable or throwaway flow sensor is an FS 200 flow sensor made by Puritan-Bennett Corporation comprising an elongated hollow plastic tube having a circular air inlet opening at one end but flared outwardly in the fashion of the bell of a trumpet at the other or air outlet end. The outlet opening is covered over with an air-resistive element in the form of a single-layered woven synthetic fabric. The threads or filaments of the fabric are woven randomly and therefore the openings or air passageways, and the resulting air flow through the air resistive fabric, may not be uniform across the entire breadth of the fabric. This may produce a non-linear relationship between air flow and air pressure. Also, the outward flare of the tube at the air discharge or outlet opening may not adequately reduce any air pressure reflections from the resistive element back to the pressure reading takeoff which may affect the pressure reading which is fed to the instrumentation.

Another commercially available device, sold under the trademark name "Respiradyne" by Chesebrough Pond's, Inc., utilizes an elongated hollow tube with a circular air inlet opening at one end and a similar circular air discharge or outlet opening at the other end with the air outlet opening covered over with an air-resistive element made from a multiple-layered fabric that is in an inverted converging cone or tent shape. Each fabric layer is made out of randomly oriented synthetic fibers or filaments. Here, again, because of the random nature of the weave of the fabric the air openings or passageways as well as the air flow may not be uniform throughout the breadth of the element. This also may produce a non-linear relationship between air flow and air pressure. Also, the converging shape of the resistive element may not adequately reduce the air pressure reflections from the air-resistive element which may reflect back to the pressure pickoff point and thereby give an incorrect reading.

SUMMARY OF THE INVENTION

The present invention utilizes an air-resistive fabric covering over the air outlet opening at one end of a hollow tube with the fabric having a multitude of substantially uniform tubular-like openings or apertures which are closely spaced and uniformly spread throughout the breadth of the fabric to produce capillary air flow which ensures a linear relationship between air flow and air pressure. Further, in the preferred embodiment the air output or outlet of the mouthpiece appears to the air flow as a uniformly diverging annular opening so there is little or no likelihood that the air flow will be affected by the shape of the outlet opening or by the nature of the resistive element to create or cause reflections back to the pressure pickoff port to give inaccurate or incorrect readings. In the preferred form, the circular opening at the opposite end of the tube from the air inlet opening is closed off with a plug which has a proportionally tapered cone section extending into the tube with the apex of the cone in line with the axis of the tube and the air outlet comprises substantially uniform, generally uniformly spaced openings through the wall of the tube which are opposite or facing the proportionally tapered cone section of the plug. In this fashion the air from the inlet opening sees a uniformly diverging annular outlet opening which is unlikely to cause any reflections back to the pressure pickoff to produce incorrect readings.

BRIEF DESCRIPTION OF THE DRAWINGS

FIGS. 1A and 1B are sectioned views of prior art commercially available disposable devices;

FIG. 2 is a sectioned view of a preferred embodiment of the instant invention;

FIG. 3 is a view of the preferred embodiment as taken along viewing line 3—3 of FIG. 2; and FIG. 4 is an exploded view of a section of the air-resistant material or fabric utilized in the preferred embodiment of the invention.

DESCRIPTION OF THE PREFERRED EMBODIMENTS

Some prior art devices are illustrated and described in the aforementioned publications. FIGS. 1A and 1B illustrate the commercially available FS 200 flow sensor made by Puritan-Bennett Corporation and the "Respiradyne" flow sensor made by Chesebrough Pond's, Inc., respectively. The former comprises a hollow tube 10 having an air inlet opening 11 at one end and is flared outward at 12 in the manner of the bell of a trumpet at the air outlet or discharge end. The air outlet opening is covered with an air-resistant material 13 comprising a fabric having randomly woven closely spaced fibers. A radially extending pressure pickoff opening or port 14 through the wall of tube 10 provides means for attaching a transducer which converts the pressure differential signal to an electrical signal which is then fed to suitable instrumentation to provide the desired readings. The FIG. 1B flow sensor comprises a hollow tube 16 with an air inlet opening 17 at one end and an air outlet opening 18 at the other end and a pressure takeoff 19 through the wall of the tube with a converging tent-shaped or inverted cone-shaped air resistant fabric 20 covering outlet opening 18. The multilayered fabric of the latter device is also made from randomly woven threads or strands and layers to produce the degree of air resistance required. The nature of the fabric and the dimensions of the element may cause anomalies in the air flow pattern which may result in less-than-accurate readings.

Turning next to FIGS. 2 and 3, the preferred embodiment of the instant invention includes a hollow elongated tube 22 made of plastic or some other suitable material having an air inlet opening 23 at one end and a radially extending pressure takeoff opening or port 24 through the side wall of tube 22 between the inlet opening 23 and the outlet. The other end of tube 22 opposite inlet opening 23 is closed off with a solid or imperforate plug or closure member 25 having a base section 26 and a proportionally tapered cone section 27 which extends from the base section 26 into the tube with the center or apex of the cone 28 generally in line with the central axis of tube 22. In the preferred embodiment illustrated in FIGS. 2 and 3, air outlet openings 30 are formed through the side wall of tube 22 at the outlet end. The size and spacing of openings 30 are a matter of choice provided certain criteria are met. For one, the openings should be substantially uniform and uniformly spaced around the periphery of the tube. For another, the tube wall support structure 35 that holds the end of the tube in place must be minimized and made very thin or narrow so that it does not significantly impede the free flow of the air and allows the air-flow out the openings 30 to be uniform. The embodiment illustrated in FIGS. 2 and 3 has three rectangular shaped openings 30 spaced around the periphery of the tube. Closure member 25 is located with respect to openings 30 so that the cone or tapered section 27 substantially extends over the length of openings 30 or, to put it another way, all of the openings 30 face the tapered section 27 over their entire lengths. In this fashion, then, as viewed from the air inlet end, the air outlet of tube 22 is a uniformly diverging annular opening for the air flow. Covering over the openings 30 is a layer of fabric 30 preferably made of polyester, having a multitude of closely spaced substantially uniform sub-miniature tubular apertures 32 which will generally produce capillary air flow. Fabric 31 may be attached to tube 22 covering openings 30 by using adhesive along its edges. The capillary air flow results in a linear relationship between the air flow and the air pressure over a wide range of air flow and will therefore result in more accurate and reliable readings similar to the honeycomb of metal tubes in the air-resistive element in the Fleisch pneumotachograph described by Dawson. However, in the instant invention the air resistant fabric is commercially available and is relatively inexpensive so that it becomes economically sound to discard the flow sensor or mouthpiece used for measuring the respiratory air flow after each use.

In order to appear to the air flow as close as possible to a uniformly diverging annular opening, the cone section 25 is preferably in the shape of a bullet or parabola and the tip or apex 28 is located transversely in line with the upstream edge of openings 30 and the cone or tapered section extends the entire length of the openings 30.

Considering the tip of the cone section as the origin (o,o,) and the "y" axis to be in line with the radius of the tube and the "x" axis to be along the central axis of the tube, the following establishes the loci of points defining the preferred form for the tapered or coned section 27 which provides the uniformly diverging opening:

Eq. (A) $y^2 = R^2 x/L$ where R is the radius of tube 22 and L is the length of openings 30.

It has been found that for satisfactory operation of a pneumotachometer constructed along the lines of the FIG. 2 embodiment, it is first necessary to establish a satisfactory ratio between the cross-section of the tube and the area of the outlet opening which will provide a reliable back pressure reading at the pressure pickoff. This is usually done experimentally, e.g., by trial and error. Once the ratio has been established, it should be maintained, i.e., it should be kept constant. Mathematically it turns out that the ratio of the areas can be reduced to a ratio of the tube radius (R) to the length of the outlet openings (L). It has been found that a suitable ratio of areas reduces to, $R/2L = C$ (Constant). Since in general for a given tube R is unchangeable, L must also remain constant which then establishes the shape of the tapered portion 27 of closure member 25 per Eq. (A) for that size (radius) tube.

Typically, for example, tube 22 may be made of a suitable plastic having a length of about 7 in., an inner diameter of about 1.18 in. and an outer diameter of about 1.25 in. The openings 30 through the wall of the tube are rectangular with an overall area of about 4 in. sq. with the downstream edge located about ½ in. from the end of tube 22. The air resistive fabric 31 is made of strands of non-hygroscopic material, such as polyester, woven to form substantially uniform tubular openings 32 through the fabric which, upon close inspection, appear to be substantially square in cross-section measuring in the range of about 17 microns on a side and in the range of about 75 microns in length, the length corresponding to the thickness of the fabric.

We claim:

1. A flow sensor for a pneumotachometer, comprising:
   an elongated hollow tubular member opening at both ends, one of said open ends comprising an air inlet for receiving air traveling longitudinally through the tubular member;
   an air outlet through the wall of said tubular member adjacent the other of said open ends;
   means extending part way into the tubular member from the other of said open ends for closing off said other open end and for diverging the longitudinal air flow from the air inlet to said air outlet;
   a thin, air-restrictive covering over said air outlet; and
   an air pressure pickoff port extending radially outward through the wall of said tubular member between the air inlet and the air outlet.

2. The invention as described in claim 1 wherein said covering comprises a thin fabric containing a multitude of closely-spaced substantially uniform sub-miniature tubular apertures.

3. The invention as in claim 1 wherein said means for diverging the longitudinal air flow and for closing off said other open end comprises a base section closing off said other open end of said tubular member and a conical proportionally tapered member extending part way into said tubular member from said base section with the apex of the tapered section located on the longitudinal axis of said tubular member.

4. The invention as in claim 3 wherein said air outlet comprises a plurality of substantially uniformly-spaced openings through the wall of said tubular member.

5. The invention as in claim 4 wherein said plurality of openings are substantially rectangular.

6. The invention as in claim 5 wherein the length of said plurality of openings are measured parallel to the tubular longitudinal axis is substantially equal to the length of the tapered member as measured along the tube longitudinal axis.

7. The invention as described in claim 6 wherein the axis of said tapered member is transversely in line with the edges of said plurality of openings which are closest to the air inlet end.

* * * * *